United States Patent
Ben Chaabane et al.

(10) Patent No.: US 10,457,925 B2
(45) Date of Patent: *Oct. 29, 2019

(54) PROCESS FOR THE PRODUCTION OF CELLULOLYTIC AND/OR HEMICELLULOLYTIC ENZYMES

(71) Applicants: Fadhel Ben Chaabane, Paris (FR); Frederic Monot, Nanterre (FR)

(72) Inventors: Fadhel Ben Chaabane, Paris (FR); Frederic Monot, Nanterre (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/684,633

(22) Filed: Aug. 23, 2017

(65) Prior Publication Data

US 2017/0349888 A1    Dec. 7, 2017

Related U.S. Application Data

(63) Continuation of application No. 13/809,734, filed as application No. PCT/FR2011/000350 on Jun. 16, 2011, now abandoned.

(30) Foreign Application Priority Data

Jul. 12, 2010 (FR) ..................... 10 02923

(51) Int. Cl.
| | |
|---|---|
| *C12N 1/16* | (2006.01) |
| *C12N 9/42* | (2006.01) |
| *C12N 1/14* | (2006.01) |
| *C12P 21/02* | (2006.01) |
| *C12N 9/24* | (2006.01) |

(52) U.S. Cl.
CPC ............ *C12N 9/2437* (2013.01); *C12N 1/14* (2013.01); *C12N 9/248* (2013.01); *C12N 9/2434* (2013.01); *C12P 21/02* (2013.01); *Y02E 50/16* (2013.01)

(58) Field of Classification Search
CPC ........ Y02E 50/16; C12N 1/16; C12N 9/2437; C12N 1/14; C12N 9/2477; C12P 7/10; C12P 2201/00; C12P 2203/00; C13K 1/02; C13K 13/00; C08L 1/02; D21C 5/005

See application file for complete search history.

(56) References Cited

U.S. PATENT DOCUMENTS 7,494,792 B2    2/2009  Warzywoda et al.
2006/0177917 A1    8/2006  Warzywoda et al.

FOREIGN PATENT DOCUMENTS

EP    1690944    8/2006

OTHER PUBLICATIONS

Chauve, M. et al., "Comparative kinetic analysis of two fungal β-glucosidases," Biotechnology for Biofuels, 2010, vol. 3, No. 3, pp. 8 pages.
Herpoël-Fimbert, I. et al., "Comparative secretome analyses of two Trichoderma reesei RUT-C30 and CL847 hypersecretory strains," Biotechnology and Biofuels, 2008, vol. 1, No. 18, 12 pages.
International Search Report for PCT/FR2011/000350; Date of the actual completion of the International Search—Sep. 13, 2011, dated Sep. 21, 2011.
Ling, M. et al., "Induction of cellulase gene transcription by a novel oligosaccharide: molasses alcohol stillage substance," World J. Microbiol Biotechnol, 2009, vol. 25, pp. 1485-1489.
Pourquié, J. et al., "Cellulase production by trichoderma reesei," Bioconversion of Forest and Agricultural Plant Residues, 1993, pp. 107-116.
Pourquié, J. et al., "Scale up of cellulase production and utilization," Biochemistry and Genetics of Cellulose Degradation, Jan. 1, 1988, pp. 72-79.

*Primary Examiner* — Lynn Y Fan
(74) *Attorney, Agent, or Firm* — Millen, White, Zelano & Branigan, PC

(57) ABSTRACT

The process for the production of cellulolytic and/or hemicellulolytic enzymes by a cellulolytic and/or hemicellulolytic microorganism according to the present invention comprises at least one phase for growth in the presence of a source of carbon and at least one phase for production in the presence of an inducing substrate, in which said inducing substrate is a mixture comprising 40% to 65% by weight of glucose or cellulosic hydrolysates, 21% to 25% by weight of lactose and 10% to 39% by weight of xylose or a solution of a lignocellulosic hemicellulosic hydrolysate, the sum of these three constituents being equal to 100%.

15 Claims, No Drawings

PROCESS FOR THE PRODUCTION OF CELLULOLYTIC AND/OR HEMICELLULOLYTIC ENZYMES

FIELD OF THE INVENTION

The invention relates to a process for the production of enzymes for the hydrolysis of lignocellulosic biomass.

PRIOR ART

The increase in bioethanol production capacity for its qualities for in biofuels is a current "hot topic". Incorporation targets are under discussion within the European Union, based on an initial proposition of 20% use of renewable energy by 2020 with an incorporation of 10% of biofuels, subject to sustainability criteria which should favour second generation biofuels produced from lignocellulosic biomass.

Lignocellulosic biomass is characterized by a complex structure constituted by three principal polymers: cellulose, hemicellulose and lignin.

Conventionally, the process for the transformation of biomass into ethanol comprises a number of steps. A pre-treatment can render cellulose and possibly hemicelluloses, which are the targets for enzymatic hydrolysis, accessible to enzymes. The pre-treatment is aimed at modifying the physical and physico-chemical properties of the lignocellulosic material with a view to improving accessibility to the cellulose trapped in the matrix of lignin and hemicellulose. The enzymatic hydrolysis step can be used to transform cellulose and hemicelluloses into sugars using cellulolytic and/or hemicellulolytic enzymes.

The sugars obtained by hydrolysis of lignocellulosic biomass are pentoses (principally xylose and arabinose), disaccharides (cellobiose) and glucose, which can be fermented by microorganisms. Glucose may, for example, be readily transformed into ethanol by the yeast *Saccharomyces cerevisiae* during the alcoholic fermentation step.

Finally, a distillation step can separate and recover the product obtained from the fermentation, i.e. ethanol in the above case, from the fermentation must.

Various technico-economic studies have demonstrated the necessity of reducing the costs linked to the enzymatic hydrolysis step in order to bring the cost of the ethanol produced to values close to that for the ethanol obtained from starch.

Currently, industrial cellulases are principally produced by a filamentous fungus, *Trichoderma reesei*, because of its high cellulase-secreting power.

One of the ways of reducing costs consists of optimizing the operating conditions for the cellulase production process in order to increase its productivity or to obtain an enzymatic cocktail with an improved specific activity.

In the presence of an inducing substrate, wild type strains of *Trichoderma reesei* have the ability to secrete an enzymatic complex which is well suited to cellulose hydrolysis. The enzymes of the enzymatic complex contain three major types of activity: endoglucanases, exoglucanases and cellobiases. Other proteins, such as xylanases, which are necessary for hydrolysis of the lignocellulosic biomass, are also produced by *Trichoderma reesei*. The presence of an inducing substrate is indispensable to the expression of cellulolytic and/or hemicellulolytic enzymes.

Regulation of the genes for cellulases on various carbon sources has been studied in detail. Glucose exerts a catabolic repression effect on the production of cellulases. This is induced in the presence of cellulose, its hydrolysis products such as cellobiose or certain oligosaccharides, in particular disaccharides such as lactose or sophorose (Ilmén et al. 1997, Appl. Environ. Microbial. Vol 63, p 1298-1306). The nature of the carbonaceous substrate has a major influence on the composition of the enzymatic complex. Thus, xylose, associated with a carbonaceous inducing substrate such as cellulose or lactose, can be used to significantly improve the "xylanase activity" when it is present in limiting concentrations of the order of 0.5 to 1 mM (Mach-Aigner et al., 2010 Applied and Environmental Microbiology, Vol 76 No 6, p 1770-1776). Dissolving residual hemicelluloses (xylanes) with xylanases could promote enzymatic hydrolysis (Vànai et al., 2010 Enzyme and Microbial Technology Vol 46 p 185-193).

In order to obtain good enzyme productivities, it is necessary to provide a source of carbon that can be rapidly assimilated in order to allow rapid growth of *Trichoderma reesei*, and an inducing substrate that can allow the expression of cellulases and secretion into the culture medium. Cellulose can play a dual role. However, it is difficult to use on an industrial scale and it has been replaced by soluble carbon sources, such as lactose, which also act as an inducing substrate.

Other sugars such as cellobiose or sophorose have also been described as inducers (Ilmen et al. (1997), Foreman et al. (2003) Biol Chem 278, p 31988-31997, Pakula et al. (2005) Microbiology, 151, p 135-143), but are too expensive to be used on an industrial scale.

In general, it has been observed that the production of cellulases by *Trichoderma reesei* with soluble substrates is much lower than that obtained on cellulose in a batch mode (i.e. in a sealed medium) because of the repressor effect of sugars that are readily assimilated at high concentrations.

Patent FR-B-2 555 603 in the name of the Applicant proposes the continuous supply of carbonaceous substrates in order to lift the catabolic repression by limiting the residual concentration in the cultures and by optimizing the quantity of sugars in order to obtain a better yield and better enzymatic productivity. The process described in this patent proposes starting to supply the substrate using soluble sugars as the source of carbon, optionally in the form of a mixture. However, a continuous supply limiting glucose or xylose not associated with lactose or with another cellulase inducer (sophorose, cellobiose, etc) cannot be used to obtain high enzyme productivity.

In industrial cellulolytic enzyme production processes, lactose remains one of the most suitable substrates. In addition to being high, its price fluctuates a great deal and represents approximately one third of the cost price of the enzymes.

One of the solutions envisaged and presented in patent EP-B-0 448 430 consists of using carbonaceous substrates obtained from a die, for example hydrolysed hemicelluloses, as a source of inducing carbon. However, the productivity remains low, at about 50% compared with the process using lactose alone as an inducing substrate.

Patent application WO 2009/026716 describes a process for the production of cellulases in which the hemicellulolytic derivatives represent more than 40% of the carbon source and the sugars inducing cellulase production represent in the range 3% to 20% of this mixture. That process can be used to produce at least twice the quantity of cellulases compared with a process using only sugars obtained from hemicelluloses. However, the cellulase production performance is still lower than a process using only lactose.

Current research shows that, in order to improve cellulolytic and/or hemicellulolytic enzyme production processes, it is necessary to develop novel inducing substrates which perform at least as well as those using lactose, and which cost less.

This constitutes the context of the present invention.

SUMMARY OF THE INVENTION

The present invention describes a process for the production of cellulolytic and/or hemicellulolytic enzymes in which the inducing substrate is a mixture of glucose, lactose and xylose.

DETAILED DESCRIPTION OF THE INVENTION

The process for the production of cellulolytic and/or hemicellulolytic enzymes by a cellulolytic and/or hemicellulolytic microorganism according to the present invention comprises at least one phase for growth in the presence of a source of carbon and at least one phase for production in the presence of an inducing substrate, in which said inducing substrate is a mixture of glucose or cellulosic hydrolysates, lactose and xylose or a solution of hemicellulolytic hydrolysates, the quantities of each of the constituents of the mixture being defined by the following limits:

40% to 65% by weight of glucose or cellulosic hydrolysates;
21% to 25% by weight of lactose; and
10% to 39% by weight of xylose or a solution of hemicellulosic hydrolysates;

the sum of these three constituents being equal to 100%.

The inducing substrate is free of any sugar other than the constituents listed above. Thus, the relative proportions of each of the constituents are selected such that the sum of the quantities by weight is equal to 100%.

Thanks to the process of the invention using a mixture of particular sugars as an inducing substrate, the final concentrations of proteins obtained are 50% to 60% higher than those obtained with lactose used as the sole production substrate. They are also approximately 3 times higher than that obtained with improved mixtures which are rich in xyloses as described in the prior art document WO 2009/026716.

The process of the present invention uses a mixture based on glucose. More than 60% of lactose, an inducer of cellulase production, can be replaced by glucose which, however, is known to be a repressor of cellulase production, with improved final performance of the inducing mixture. Glucose is much cheaper than lactose and its solubility in water is approximately 3 times higher. Thus, it is possible to reduce the volumes employed. Thus, in this process, glucose is not only used in the growth phase, but also in the production phase in an amount of 60% of the mixture constituting the inducing substrate.

The glucose used in the mixture of sugars may also be replaced by glucose obtained from the cellulose enzymatic hydrolysis step, i.e. obtained directly from the process for the transformation of lignocellulosic biomass into ethanol. This contributes to reducing the cost of enzyme production by using co-products from the process. Thus, they are termed cellulosic hydrolysates.

The xylose used in the mixture constituting the inducing sugar may be replaced by a solution of hemicellulolytic hydrolysates obtained from the process for the transformation of lignocellulosic biomass into ethanol, and in particular obtained from pre-treatment of the biomass.

Furthermore, the possibility of using a very highly concentrated mixture of sugars can advantageously limit the risk of contamination.

The fact that xylose is added to the mixture constituting the inducing substrate means that the xylanase activity of the final enzymatic cocktail is greatly increased. The xylose may advantageously be replaced by a hemicellulosic hydrolysate solution obtained from the hydrolysis of hemicelluloses during pre-treatment of the lignocellulosic biomass in second generation biofuel production processes; it may be concentrated if necessary.

Preferably, the mixture constituting the inducing substrate comprises 50% to 65% by weight of glucose or cellulosic hydrolysates, 22% to 24% by weight of lactose and 15% to 25% by weight of xylose or a solution of hemicellulosic hydrolysates, optionally obtained from a pre-treatment of the lignocellulosic biomass, the sum of the constituents being equal to 100%.

Highly preferably, the inducing substrate is a mixture constituted by 60% by weight of glucose or cellulosic hydrolysates, 23% by weight of lactose and 17% by weight of xylose or hemicellulosic hydrolysates.

The carbonaceous substrate used during the growth phase is selected from glucose, xylose, lactose, residues obtained after ethanolic fermentation of monomeric sugars of the enzymatic hydrolysates of cellulosic biomass and/or an unrefined extract of hydrosoluble pentoses possibly deriving from the pre-treatment of a cellulosic biomass.

Highly preferably, the growth substrate is glucose.

The industrial strains used belong to the species *Trichoderma reesei*, modified in order to improve the cellulolytic and/or hemicellulolytic enzymes by mutation-selection processes. An example which can be cited is the strain IFP CL847. Strains improved by genetic recombination techniques may also be used. They have to be deleted for catabolic repression by glucose (Δ CRE1); an example is CL847.

These strains are cultivated in agitated, aerated bioreactors under conditions which are compatible with their growth and the production of enzymes. The conditions are such that the pH is adjusted to between 3.5 and 6 and the temperature is in the range 20° C. to 35° C. Preferably, a pH of 4.8 and a temperature of 27° C. are selected during the growth phase and a pH of 4 and a temperature of 25° C. are selected during the production phase. The degree of aeration, expressed as the volume of air per volume of reaction medium per minute, or vvm, applied during the process is in the range 0.3 to 1.5 $min^{-1}$, and the rate of rotation, rpm, must allow the $O_2$ pressure to be adjusted to between 20% and 60%. Preferably, an aeration of 0.5 vvm and agitation to allow the $O_2$ pressure to be adjusted to 30% are selected.

Depending on its nature, the carbonaceous substrate selected to obtain the biomass is introduced into the bioreactor before sterilization, or is sterilized separately and introduced into the bioreactor after sterilization thereof in order to produce an initial sugar concentration of 15 to 60 g/L.

In view of the production phase, an aqueous solution containing the inducing substrate constituted by a glucose/lactose/xylose mixture or hemicellulose hydrolysate solution selected for the enzyme production phase is prepared in a concentration of 350 to 600 g/L in the feed solution used.

Preferably, the concentration is in the range 450 to 550 g/L.

The aqueous solution is injected after the initial substrate has been exhausted in order to provide an optimized quantity. The flow rate at which the solution is supplied is 30 to 45 mg per gram of cells per hour.

The residual sugar concentration in the culture medium is less than 1 g/L during the production phase (fed-batch) in order to limit the production of biomass. Preferably, this concentration is less than 0.5 g/L, still more preferably less than 0.1 g/L.

EXAMPLES

In the examples which follow, Example 1 presents a culture using glucose as the carbonaceous substrate during the growth phase and the production phase. This example demonstrates the low production of proteins obtained when this sugar is used as the sole carbonaceous substrate even if the flow is limiting during the fed-batch phase (residual concentration of glucose close to 0). The second example represents the reference fermentation using lactose as the carbonaceous substrate during the growth phase and the production phase which allows high protein production. Example 3 reproduces an experiment using a mixture in the production phase as described in patent application WO 2009/026716 containing a high proportion of xylose allowing, according to the authors, the cellulase production to be greatly increased compared with an experiment in which xylose or hemicellulosic derivatives are used as the sole carbonaceous substrates. Examples 4 to 6 are those of the patent, in accordance with the process of the present invention.

Example 1: Production of Enzymes on Glucose (Not in Accordance with the Invention)

The production of cellulases was carried out in a mechanically stirred bioreactor. The mineral medium had the following composition: KOH 1.66 g./L, $H_3PO_4$ 85% 2 mL/L, $(NH_4)_2SO_4$ 2.8 g/L, $MgSO_4.7\ H_2O$ 0.6 g/L, $CaCl_2$ 0.6 g/L, $MnSO_4$ 3.2 mg/L, $ZnSO_4.7\ H_2O$ 2.8 mg/L, $CoCl_2.10H_2O$ 4.0 mg/L, $FeSO_4.7\ H_2O$ 10 mg/L, Corn Steep 1.2 g/L, anti-foaming agent 0.5 mL/L.

The bioreactor containing the mineral medium was sterilized at 120° C. for 20 minutes; the glucose carbonaceous source was sterilized from 120° C. for 20 minutes then added to the bioreactor under sterile conditions in order to produce a final concentration of 30 g/L. The bioreactor was primed to 10% (v/v) with the liquid pre-culture of the CL847 strain of *Trichoderma reesei*. The mineral medium of the pre-culture was identical to that of the bioreactor apart from adding potassium phthalate in a concentration of 5 g/L to buffer the pH. Growth of the fungus in pre-culture was carried out using glucose as the carbonaceous substrate at a concentration of 30 g/L. Growth of the inoculum lasted 2 to 3 days and was carried out at 28° C. in a shaker incubator. Transfer to the bioreactor was carried out if the residual concentration of glucose was less than 15 g/L.

The experiment carried out in the bioreactor comprised two phases:
  a phase for growth on a glucose carbonaceous substrate (initial concentration=30 g/L) at a temperature of 27° C. and a pH of 4.8 (regulated with 5.5 M ammonia). Aeration was at 0.5 vvm and agitation was increased between 200 and 800 rpm as a function of the $pO_2$ (dissolved oxygen pressure), which was kept above 30%;
  an enzyme production phase. When the initial substrate of the fermenter was exhausted, the 250 g/L glucose solution was injected continuously at a flow rate of 30 to 40 mg per gram of cells per hour up to 164 hours. The temperature was reduced to 25° C. and the pH to 4 until the end of culture. The pH was adjusted by adding a 5.5 N ammonium solution which provided the nitrogen necessary for synthesis of the excreted proteins. The dissolved oxygen content was kept above 15% to 20% by adjusting the aeration and agitation.

Enzyme production was followed by assaying the extracellular proteins using the Lowry method and BSA standard, after separation from the mycelium by filtering or centrifuging. The cellulolytic activities which were determined were:
  the filter paper activity (FPU=filter paper unit), which meant that the overall activity of the endoglucanase and exoglucanase enzymatic pool could be assayed;
  the aryl β-glucosidase and xylanase activities for the specific activities.

The FPU activity was measured on Whatman No 1 paper (procedure recommended by the IUPAC Biotechnology Commission) at an initial concentration of 50 g/L; the test sample from the enzymatic solution to be analysed which liberated the equivalent of 2 g/L of glucose (colorimetric assay) in 60 minutes was determined. The principle of filter paper activity is to determine, by DNS (dinitrosalicylic acid) assay, the quantity of reduced sugars obtained from a Whatman No 1 paper (procedure recommended by the IUPAC Biotechnology Commission).

The substrate used to determine the aryl β-glucosidase activity was p-nitrophenyl-β-D-glucopyranoside (PNPG). It is cleaved by β-glucosidase to liberate p-nitrophenol. One aryl β-glucosidase activity unit is defined as the quantity of enzyme necessary to produce 1 μmole of p-nitrophenol from PNPG per minute and is expressed in IU/ml. The principal of xylanase activity assay resides in determining, by DNS assay, the quantity of reduced sugars obtained from the hydrolysed xylanase solution. This assay method uses the reducing properties of the sugars, principally xylose. The xylanase activity is expressed in IU/ml, and corresponds to the quantity of enzyme necessary to produce 1 μmole of xylose per minute.

The specific activities were obtained by dividing the activities expressed in IU/ml by the concentration of proteins. They are expressed in IU/mg.

The analytical determinations on the final must of Example 1 produced the following results:
The analytical determinations of the final must produced the following results:
Biomass 15.2 g/L
Proteins 2.9 g/L
FPU 1.4 IU/mL
Xylanase 29.1 IU/mg
Specific β-glucosidase 0.35 IU/mg The CL847 strain was presented as being derepressed to the catabolic repression exerted by glucose on the production of cellulase (it is deleted from the CRE1 gene). It appears that even for a fed-batch reaction carried out under glucose limitation conditions, the final production of proteins is very low.

Example 2: Production of Enzymes on Lactose (Not in Accordance with the Invention)

Enzyme production was carried out under the same conditions as in Example 1. The carbonaceous substrate during the growth and production phases was pure lactose. Lactose is an important inducer in cellulase production. It is this substrate which is the most widely used for the production of cellulases on an industrial scale.

After 30 hours of growth, after exhausting the initial substrate, the 250 g/L fed-batch solution was injected continuously at a flow rate of 35 mg per gram of cells per hour up to 164 hours.

The analytical determinations of the final must produced the following results:
Biomass 13.5 g/L
Proteins 37.8 g/L
FPU 22.1 IU/mL
Xylanase 408.5 IU/mg
Specific β-glucosidase 0.96 IU/mg Example 3: Production with Mixture of 97% Xylose/3% Sugars Inducing the Production of Cellulases ClC (Not in Accordance with the Invention)

The experiment was carried out under the same conditions as in Example 1, using pure xylose as the sole carbonaceous substrate during the growth phase, and in the production phase the 97% xylose/3% ClC mixture presented in patent application WO 2009/026716 A1. ClCs (sugars inducing the production of cellulases) are a mixture of sugars allowing the induction of cellulase production. Its composition was as follows: 56% gentiobiose, 14% sophorose, 10% trehalose, 6% cellobiose, 6% maltotriose, 8% glucose.

After exhausting the initial substrate, the 360 g/L 97% xylose/3% ClC mixture was injected, following the recommendations described, at a flow rate of 0.4 g of carbon/L/h.

The analytical determinations of the final must produced the following results:
Biomass 14.3 g/L
Proteins 18.7 g/L
FPU 6.4 IU/ml
Xylanase 6000.1 IU/mg
Specific FPU 0.34 IU/mg
Specific β-glucosidase 1.15 IU/mg The final protein production was close to that presented in WO 2009/026716 A1 where the authors obtained a final concentration of proteins of 25 g/L with the P59G strain. The FPase specific activity (0.34 IU/mg) was low, while the xylanase activity was very high.

Example 4: Production with Lactose (23%)/Glucose (60%)/Xylose (17%) Mixture at 500 g/L (In Accordance with the Invention)

The experiment of Example 4 was carried out under the same conditions as in Example 1 with glucose as the carbonaceous substrate for growth in an amount of 60 g/L. During the fed-batch production phase, we then used a solution in which three carbonaceous substrates were mixed in the following proportions: lactose (23%)/glucose (60%)/xylose (17%), at a concentration of 500 g/L. This mixture was injected at 45 mg/g/h. The analytical determinations of the final must produced the following results:
Biomass 26.1 g/L
Proteins 61.8 g/L
FPU 33.7 IU/ml
Xylanase 4017 IU/mg
Specific FPU 0.55 IU/mg
Specific β-glucosidase 1.2 IU/mg The final protein production was more than 3 times higher than that of Example 3. The filter paper activity, which is an indicator of cellulase activity, was approximately 5 times higher.

The xylanase activity was 10 times higher than that of Example 2 carried out with lactose as the sole growth and production carbonaceous substrate, but approximately 50% lower than that of Example 3.

Example 5: Use of Lactose (23%)/Glucose (60%)/C5 Sugar Solution (17%) Mixture, at 500 g/L (In Accordance with the Invention)

Example 5 was carried out under the same conditions as Example 4. The glucose was used during the growth phase, at a concentration of 15 g/L. The xylose of the fed-batch solution was replaced by a solution of soluble hemicellulosic solution or C5 sugar solution obtained from a wheat straw impregnated with 0.08 N sulphuric acid and pre-treated by steam explosion (19 bar, 5 minutes). The mixture was injected at 30 mg/g/h for 170 h.

The analytical determinations of the final must produced the following results:
Biomass 19.1 g/L
Proteins 57.3 g/L
FPU 25.1 IU/ml
Xylanase 1151 IU/mg
Specific FPU 0.44 IU/mg
Specific β-Glucosidase 1.4 IU/mg This experiment allowed the protein production to be increased by more than 50% compared with Example 2 and the xylanase activity was almost 3 times better. The majority of lactose was replaced by glucose and C5 sugar solution during the growth phase and production phase. The concentration of glucose during the growth phase was reduced compared with Example 4, by 60 to 15 g/L. The concentration of biomass was reduced from 26 to 19 g/L but this had little impact on the final concentration of proteins (7% lower). Thus, use of the sugars was optimized and the cost of the carbon source was considerably reduced.

Example 6: Use of Lactose (23%)/C6 Hydrolysates (56%)/Xylose (21%) Mixture, 500 g/L (In Accordance with the Invention)

Example 6 was carried out under the same conditions as Example 4. The glucose was used during the growth phase, at a concentration of 15 g/L. The glucose of the fed-batch solution was replaced by a solution of hydrolysate obtained from the enzymatic hydrolysis of a wheat straw impregnated with 0.08 N of sulphuric acid and pre-treated by steam explosion (19 bar, 5 minutes). The enzymatic hydrolysis of the wheat straw was carried out at 50° C. and at a pH of 4.8. It resulted in hydrolysis of 95% of the cellulose into glucose.

Lactose and xylose were dissolved in this solution so as to result in a mixture:
Lactose (23%)/C6 hydrolysates (56%)/xylose (21%), at 500 g/L.

The mixture was injected at 30 mg/g/h for 170 h during the fed-batch phase.

The analytical determinations of the final must produced the following results:
Biomass 16.1 g/L
Proteins 43.1 g/L
FPU 31.4 IU/ml
Xylanase 6595.1 IU/mg
Specific FPU 0.73 IU/mg
Specific β-glucosidase 1.2 IU/mg The enzymatic cocktail obtained was very high quality, since the final FPase activity was close to the activity obtained in Example 4 even if the protein concentration was lower. The final FPase activity was approximately 5 times higher than that obtained with Example 3 and approximately 50% higher than that obtained during Example 2 where lactose was used as the sole carbonaceous substrate during the fed-batch phase.

The invention claimed is:

1. A process for the production of cellulolytic and/or hemicellulolytic enzymes by a cellulolytic and/or hemicellulolytic microorganism, comprising
   (a) growing the microorganism in a culture medium in the presence of a source of carbon;
   (b) inducing the production of the enzymes by the microorganism in the presence of an inducing substrate, wherein said inducing substrate is a mixture of cellulosic hydrolysates, lactose and a solution of hemicellulosic hydrolysates, the quantities of each of the constituents of the mixture are defined by the following limits:
      50% to 65% by weight of cellulosic hydrolysates;
      22% to 24% by weight of lactose; and
      15% to 25% by weight of a solution of hemicellulosic hydrolysates;
   the sum of these three constituents being equal to 100%, and wherein the microorganism belongs to the species *Trichoderma reesei* which is deleted for catabolic repression by glucose,
   wherein the inducing substrate is supplied in a solution having a concentration of 350 to 600 g/L, and
   wherein both the source of carbon and the inducing substrate comprise sugar, and wherein the cellulosic hydrolysates and the solution of hemicellulosic hydrolysates are obtained from a pretreatment of lignocellulosic biomass, and/or the cellulosic hydrolysates are obtained directly from a process for the transformation of lignocellulosic biomass into ethanol.

2. The process according to claim 1, wherein the inducing substrate is supplied in a solution having a concentration in the range of 450 to 550 g/L.

3. The process of claim 1, wherein the inducing substrate is a mixture of 60% by weight of cellulosic hydrolysates, 23% by weight of lactose and 17% by weight of a solution of hemicellulosic hydrolysates.

4. The process of claim 1, wherein the carbon source in (a) is glucose, xylose, lactose, residues obtained after ethanolic fermentation of monomeric sugars of the enzymatic hydrolysates of cellulosic biomass and/or an unrefined extract of hydrosoluble pentoses derived from pre-treatment of a cellulosic biomass.

5. The process of claim 1, wherein growth step (a) is conducted at a pH of 3.5 to 6 and the temperature is 20° C. to 35° C.

6. The process of claim 1, wherein in (b) the induction solution is introduced at a flow rate of 30 to 45 mg per gram of cells per hour.

7. The process according to claim 1, wherein the residual concentration of sugar in the culture medium during the production phase is less than 1 g/L.

8. The process of claim 1, wherein the residual concentration of sugar in the culture medium during induction step (b) is less than 0.5 g/L.

9. The process of claim 1, wherein the residual concentration of sugar in the culture medium during induction step (b) is less than 0.1 g/L.

10. The process of claim 1, wherein the constituent of the inducing substrate that is 15% to 25% by weight of a solution of hemicellulosic hydrolysates consists essentially of xylose.

11. The process of claim 1, wherein the production step is performed in a fed-batch reactor.

12. The process of claim 1, wherein the cellulosic and/or hemicellulosic hydrolysate inducers are obtained from lignocellulosic biomass and are concentrated prior to addition to step (b).

13. The process of claim 1, wherein the cellulosic hydrolysates comprise glucose.

14. The process of claim 1, wherein a specific beta glucosidase activity of at least 1.2 IU/mg is achieved.

15. A process for the production of cellulolytic and/or hemicellulolytic enzymes by a cellulolytic and/or hemicellulolytic microorganism, comprising
   (a) growing the microorganism in a culture medium in the presence of a source of carbon;
   (b) inducing the production of the enzymes by the microorganism in the presence of an inducing substrate, wherein said inducing substrate is a mixture of cellulosic hydrolysates, lactose and a solution of hemicellulosic hydrolysates,
   wherein
      the cellulosic hydrolysates and the hemicellulosic hydrolysates are obtained from a pre-treatment of lignocellulosic biomass, and/or
      the cellulosic hydrolysates are obtained directly from a process for the transformation of lignocellulosic biomass into ethanol,
   wherein the quantities of each of the constituents of the mixture are defined by the following limits:
      50% to 65% by weight of cellulosic hydrolysates;
      22% to 24% by weight of lactose; and
      15% to 25% by weight of a solution of hemicellulosic hydrolysates;
   the sum of these three constituents being equal to 100%,
   wherein
   the microorganism belongs to the species *Trichoderma reesei* which is deleted for catabolic repression by glucose,
   the cellulosic and/or hemicellulosic hydrolysate inducers obtained from lignocellulosic biomass are concentrated prior to addition to step (b), whereby the inducing substrate is supplied in a solution having a concentration of 350 to 600 g/L, and
   both the source of carbon and the inducing substrate comprise sugar, whereby a specific beta glucosidase activity of at least 1.2 IU/mg is achieved.

* * * * *